United States Patent [19]
Olsson et al.

[11] Patent Number: 5,400,777
[45] Date of Patent: Mar. 28, 1995

[54] VENTILATOR

[75] Inventors: Sven-Gunnar Olsson, Arloev; Bo Dahlstroem, Vaellingby; Goeran Rydgren, Bunkeflostrand; Goeran Cewers, Lund, all of Sweden

[73] Assignee: Siemens Aktiengesellschaft, Munich, Germany

[21] Appl. No.: 46,898

[22] Filed: Apr. 15, 1993

Related U.S. Application Data

[63] Continuation of Ser. No. 775,475, Oct. 15, 1991, abandoned.

[30] Foreign Application Priority Data

Oct. 31, 1990 [SE] Sweden .................. 9003466

[51] Int. Cl.⁶ .............................................. A61M 16/00
[52] U.S. Cl. ...................... 128/204.18; 128/204.21; 128/204.23
[58] Field of Search ............ 128/204.18, 204.21, 128/204.23; 364/180, 182

[56] References Cited

U.S. PATENT DOCUMENTS

| | | | |
|---|---|---|---|
| 3,322,994 | 5/1967 | Dever et al. | 364/180 |
| 3,582,631 | 6/1971 | Rijnsdorp | 364/180 |
| 3,648,032 | 3/1972 | Gineste | 364/180 |
| 3,657,524 | 4/1972 | Bakke | 364/182 |
| 3,665,172 | 5/1972 | Spaargaen et al. | 364/180 |
| 3,834,381 | 9/1974 | Peterson | 128/204.21 |
| 3,961,627 | 6/1976 | Ernst et al. | 128/204.21 |
| 3,984,665 | 10/1976 | Shriver et al. | 364/180 |
| 4,191,995 | 3/1980 | Farrow | 364/182 |
| 4,323,064 | 4/1982 | Hoenig et al. | 128/204.21 |
| 4,481,944 | 11/1984 | Bunnell | 128/204.18 |
| 4,587,967 | 5/1986 | Chu et al. | 128/204.21 |
| 4,783,741 | 11/1988 | Mitterauer | 364/413.01 |
| 4,957,107 | 9/1991 | Sipin | 128/204.21 |
| 5,107,830 | 4/1992 | Younes | 128/204.21 |

OTHER PUBLICATIONS

The New Generation of Mechanical Ventilators, Spearman et al Respiratory Care, Jun. 1987, vol. 32, No. 6, pp. 403–418.
New Generation Ventilators, Berstein et al, Anaesth, Intens. Care. vol. 14, 1986, pp. 293–305.
Brochure for 720 Microprocessor Ventilator, Puritan-Bennett Corp.
"Gebrauchsanweisung" (User's manual) for Servo Ventilator 900 C of Siemens.

*Primary Examiner*—Edgar S. Burr
*Assistant Examiner*—Aaron J. Lewis
*Attorney, Agent, or Firm*—Hill, Steadman & Simpson

[57] ABSTRACT

A ventilator to be connected to the airways of a human or an animal includes several functional units, each functional unit being controlled and/or supervised by a separate microprocessor. At least one of the functional units has an analog control unit whereby the microprocessor only compensates for the coarseness in the regulating function of the analog control unit to increase the accuracy. This makes the ventilator efficient, accurate and safe.

4 Claims, 1 Drawing Sheet

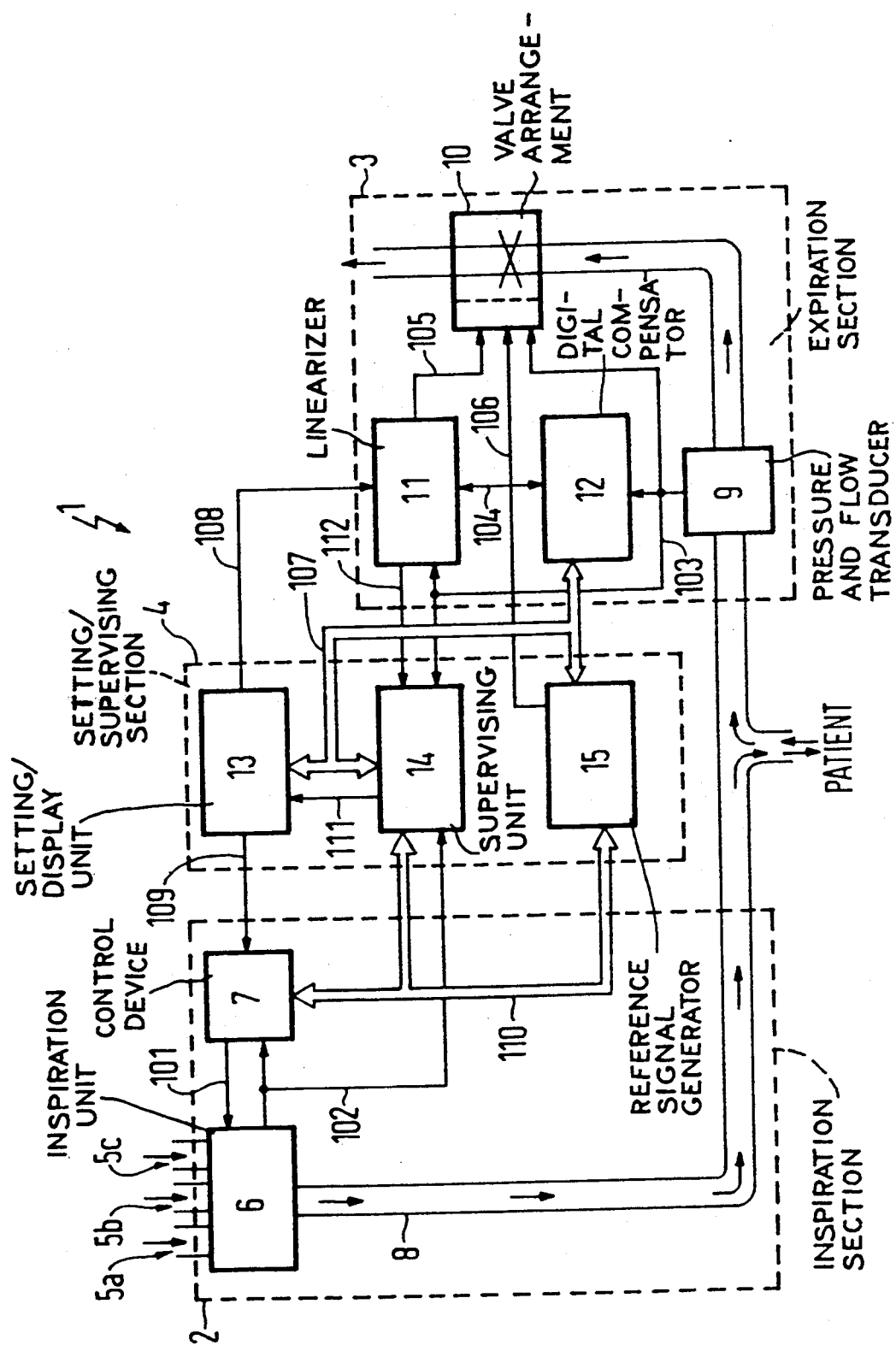

VENTILATOR

This is a continuation of application Ser. No. 775,475, filed Oct. 15, 1991, now abandoned.

BACKGROUND OF THE INVENTION

1. Field of the Invention

The invention relates to a ventilator to be connected to the airways of a human or of an animal for supplying and emitting respiratory gas to and from the airways, according to a predetermined pattern, which is dependent on at least one parameter, the ventilator having an analog control unit, which, depending on the parameter, regulates the supplying and/or the emitting of the respiratory gas so that a predetermined pattern is substantially maintained.

The invention also relates to a ventilator, of the type having several functional units, which enable the ventilator to supply and/or emit respiratory gas following a predetermined pattern, and a microprocessor which controls and/or supervises at least one of the functional units.

2. Description of the Prior Art

A known ventilator (Servo Ventilator 900C, Gebrauchsanweisung Publ. No. AG 11884, October 1988) has an expiration section with an expiration valve, which opens and closes by means of an electromagnet. Thereby, a desired pressure can be maintained in the expiration section of the ventilator. The electromagnet is controlled by an analog control unit which, depending on the existing air pressure, controls the position of the expiration valve. The advantage of the analog control unit is that it quickly adjusts to the desired regulation level, but it is not very accurate for maintaining a constant desired pressure.

Another known ventilator (7200 Series Microprocessor Ventilator, Puritan Bennett, Form No. AA-213, May 83) has a microprocessor that controls and supervises substantially all functions of the ventilator. For example, the pressure in the expiration section may be maintained with high accuracy at the desired value. On the other hand, the complexity of the system slows down a desired change of the pressure in the expiration unit because the microprocessor moves towards the new position of equilibrium at a slow pace. Further, the ventilator is extremely vulnerable. If the microprocessor would cease to function for any reason, the functional units of the ventilator will then also cease to operate, and the result may be injurious or fatal for a patient connected to the ventilator.

SUMMARY OF THE INVENTION

It is therefore an object of the present invention to provide a ventilator in which the desired values, such as flow or pressure, can be obtained quickly and maintained with high accuracy, and also have increased safety for the patient.

The above object is achieved in accordance with the principles of the present invention by providing a ventilator of the type described above with a digital control unit which, depending on the parameter and the regulation of the analog control unit, compensates for the coarseness in the regulating function of the control unit so that the predetermined pattern is maintained almost in its entirety.

Hereby, the advantages of the rapid analog adjustment and the accurate digital adjustment are combined.

Since the digital unit only compensates for the fault of the regulation of the analog unit, the ventilator will be fairly insensitive to failures in the digital unit. Should the digital unit fail, the function of the ventilator would not be inferior to a system controlled by only an analog control unit. The digital control unit preferably is a microprocessor.

Alternatively, in a ventilator of the second type described above, the problem is solved by providing a further microprocessor which controls and/or supervises at least one of the other functional units.

This decreases the risk of having the entire ventilator fail if a microprocessor ceases to function. By distributing the tasks of the microprocessors correctly, it is possible to maintain the essential life supporting functions even if a microprocessor ceases to function, and the patient will not be exposed to any danger. Further, each microprocessor can be specialized for its function and thereby be able to individually work faster than a central microprocessor, whereby the speed of the system also increases.

For optimal function, the microprocessors should exchange information with each other, and this may be done digitally, in analog form, or both. The important goal is to prevent erroneous signals from a failed microprocessor from disturbing a functioning microprocessor. This may be done, for example, by having the functioning microprocessor ignore the information from the failed microprocessor if it falls outside a specific interval that is dependent on other information in the microprocessor.

By combining the two alternative solutions, a much safer ventilator is provided, which is fast and accurate.

DESCRIPTION OF THE DRAWINGS

A block diagram of a ventilator constructed in accordance with the principles of the present invention is shown in the single figure.

DESCRIPTION OF THE PREFERRED EMBODIMENTS

The figure shows a simplified diagram of a ventilator 1 according to the invention. The ventilator 1 includes an inspiration section 2, an expiration section 3 and a setting/supervising section 4. Air and possible additional gases enter the inspiration section 2 under high pressure through the gas inlets 5a, 5b and 5c and pass through an inspiration unit 6, in which the respiratory gas is mixed to correct proportion and its pressure and flow adjusted by means of a set of valves. In the inspiration unit 6, there are also a bacteria filter, a pressure transducer, a flow transducer, an oxygen transducer, a safety valve, etc.

There are therefore several functions that need to be maintained, e.g., keeping the mixture of gases constant. This is achieved by a functional unit, which comprises valves at the gas inlets 5a, 5b and 5c. Another functional unit may supervise the mixture of gases and sound an alarm if the mixture gets out of proportion. Thereby, the safety for the patient may be optimized.

In this embodiment, the inspiration unit 6 with its functional units is controlled by a control device 7, which provides instructions for the inspiration unit 6 via a line 101 and which receives information from the inspiration unit 6 via a line 102. The line 102 also provides the information to the setting/supervising section 4, which will be described in more detail below. From the inspiration unit 6, the respiratory gas is led through a tube 8 to the airways of a patient.

In the expiration section 3, the respiratory gas is conducted away from the airways of the patient through the tube 8 and out to the surrounding area. In its outward passage, the respiratory gas will pass through a pressure and flow transducer 9 and a valve arrangement 10. By controlling the valve arrangement 10 make the tube more or less closed, a desired pressure can be maintained in the expiration section 3. Measured values of pressure and flow are transferred through a line 103 to an analog linearizer 11, a digital compensator 12 and to a servo unit in the valve arrangement 10. The line 103 also leads to the setting/supervising section 4, which is described in more detail below. The analog linearizer 11 is connected with the digital compensator 12 via a line 104, with the valve arrangement 10 via a line 105 and with the setting/supervising section 4, which is described in more detail below.

The setting/supervising section 4 has a setting/display unit 13, a supervising unit 14 and a reference signal generator 15. A data bus 107 connects the setting/display unit 13, the supervising unit 14, the reference signal generator 15 and the digital compensator 12 with each other. These connections may also be analog. The setting/display unit 13 can also send information to the analog linearizer 11 via a line 108 and to the control device 7 via a line 109 and receive information from the supervising unit 14 via a line 111. The supervising unit 14 can further, via the line 102, as mentioned above, receive information from the inspiration unit 6 and may also receive information from the pressure-and flow transducer 9 via the line 103 and from the analog linearizer 11 via a line 112. The reference signal 1 generator 15 may, via a line 106, send signals to the valve arrangement 10. Finally, the control device 7, the supervising unit 14 and the reference signal generator 15 are connected with a data bus 110. This data bus 110 may also be replaced by analog connections.

When a patient is connected to the ventilator 1, a suitable pattern is entered and is set by the setting/display unit 13, which pattern is tracked by the ventilator and adapted to the patient. The set values are transferred to a microprocessor in the setting/display unit 13, where they can be transferred further in digital form via the data bus 107. Some of the set values are also transferred in analog shape through the respective lines 108 and 109 to the analog linearizer 11 and the control device 7. The reference signal generator 15, which may be a microprocessor, calculates, based on the settings made, the breathing curve to be tracked by the inspiration section 2 and transfers this information to a microprocessor in the control device 7 via the data bus 110. The control device 7 also includes an analog control unit, which has been provided information via the line 109. It is the task of the microprocessor to compensate for any fault in the regulation of the analog control unit.

The control of the valve arrangement 10 in the expiration section 3 takes place in a similar way. The reference signal generator 15 sends a signal to the valve arrangement 10. The signal is compared with the actual pressure obtained from the pressure and flow transducer 9. To increase the speed of the control of the valve arrangement 10, a digitally compensated signal is also sent from the analog linearizer 11 to the valve arrangement 10. The digitally compensated signal is obtained by the analog linearizer 11 by first linearizing the flow value from the pressure and flow transducer 9. This linearization is sent to the digital compensator 12, which may be a microprocessor, where a compensation is calculated and sent back to the analog linearizer 11 and added to its linearizing signal. The digitally compensated signal is also transferred to the supervising unit 14. The digital compensator 12 compensates for, among other things, the mixture of the gas (viscosity), the pressure of the surrounding area and the signal from the analog linearizer 11.

The supervising unit 14 has mainly two tasks: one is to provide the setting/display unit 13 with the actual measured values in the ventilator and the other is to sound an alarm as soon as the measured values differ too much from the set values. A microprocessor in combination with analog back-up systems makes the supervising safe and accurate.

The ventilator 1 in this embodiment has a total of five microprocessors. They are, as described above, located in the setting/display unit 13, in the reference signal generator 15, in the control unit 7, in the digital compensator 12 and in the supervising unit 14. The microprocessors basically operate independently of each other but do exchange information for an optimal function. As mentioned previously, the exchange of information may be purely digital, purely analog or a combination of both. It is possible to have one or several of the microprocessors out of order without severe damage to the function of the ventilator 1. If, for example, the microprocessor in the setting/display unit 13 ceases to function, the worst that can happen is that the compensation in the control device 7 and the digital compensator 12 becomes a bit less accurate. This can happen because the microprocessor may transmit completely wrong signals when it has ceased to function. But, because the settings made also have been provided analogously through the setting of the potentiometers, the coarse regulation of the analog control will not be affected. The supervising unit 14, however, will sound an alarm, which means that a microprocessor has ceased to function and the ventilator can then be replaced and repaired at a suitable time.

Although modifications and changes may be suggested by those skilled in the art, it is the intention of the inventors to embody within the patent warranted hereon all changes and modifications as reasonably and properly come within the scope of their contribution to the art.

We claim as our invention:

1. A respiratory ventilator for connection to the airways of a human or of an animal for supplying and receiving respiratory gas to and from the airways, according to a predetermined pattern, which is dependent on at least one parameter, said ventilator comprising:

means for measuring said parameter and generating a measured parameter signal;

analog control means, connected to said means for measuring and directly supplied with said measured parameter signal, for regulating at least one of the supplying or the receiving of the respiratory gas by analog regulation based on said measured parameter signal so that said predetermined pattern is approximately maintained;

digital control means, connected to said means for measuring and directly supplied with said measured parameter seperately from said analog control means, for digitally regulating at least one of the supplying or the receiving of the respiratory gas based on said measured parameter signal and the analog regulation by digitally compensating for deviations from said predetermined pattern in the regulating by the analog control means so that the predetermined pattern is substantially fully maintained; and said analog control means operating means independently of said digital control means so that failure of said digital control means does not affect operation of said analog control means.

2. A respiratory ventilator as claimed in claim 1, wherein said digital control means is a microprocessor.

3. A respiratory ventilator as claimed in claim 1 further comprising a plurality of said analog control means.

4. A respiratory ventilator as claimed in claim 3 wherein said digital control means includes a separate microprocessor for each analog control means, each microprocessor compensating for deviations from said predetermined pattern in the regulating by the analog control means associated therewith.

* * * * *